(12) United States Patent
Lin et al.

(10) Patent No.: US 12,106,589 B2
(45) Date of Patent: Oct. 1, 2024

(54) CROSS-MEDIA KNOWLEDGE SEMANTIC REPRESENTATION METHOD AND APPARATUS

(71) Applicant: ZHEJIANG LAB, Zhejiang (CN)

(72) Inventors: Feng Lin, Hangzhou (CN); Yunhe Pan, Hangzhou (CN)

(73) Assignee: ZHEJIANG LAB, Hangzhou (CN)

( * ) Notice: Subject to any disclaimer, the term of this patent is extended or adjusted under 35 U.S.C. 154(b) by 0 days.

(21) Appl. No.: 18/491,818

(22) Filed: Oct. 23, 2023

(65) Prior Publication Data
US 2024/0046675 A1    Feb. 8, 2024

Related U.S. Application Data

(63) Continuation of application No. PCT/CN2022/099377, filed on Jun. 17, 2022.

(51) Int. Cl.
*G06V 20/70*    (2022.01)
*G06F 40/30*    (2020.01)
*G16H 30/40*    (2018.01)

(52) U.S. Cl.
CPC .............. *G06V 20/70* (2022.01); *G06F 40/30* (2020.01); *G16H 30/40* (2018.01); *G06V 2201/03* (2022.01)

(58) Field of Classification Search
CPC .... G06V 20/70; G06V 2201/03; G06V 20/46; G06V 10/44; G06V 10/462; G06V 10/70;
(Continued)

(56) References Cited

U.S. PATENT DOCUMENTS 7,437,004 B2 * 10/2008 Baatz ...................... G06T 7/174
707/999.001
2005/0283752 A1 * 12/2005 Fruchter ............. G06F 16/7837
700/88
(Continued)

FOREIGN PATENT DOCUMENTS

| CN | 104574507 A | 4/2015 |
| CN | 112991479 A | 6/2021 |
| CN | 113192069 A | 7/2021 |
| CN | 114300097 A | 4/2022 |
| CN | 114533111 A | 5/2022 |
| EP | 3185135 A1 * | 6/2017 |

OTHER PUBLICATIONS

International Search Report (PCT/CN2022/099377); Date of Mailing: Nov. 25, 2022.

*Primary Examiner* — Jose L Couso
(74) *Attorney, Agent, or Firm* — W&G Law Group

(57) ABSTRACT

A cross-media knowledge semantic representation method and apparatus. The method comprises: performing data acquisition according to a preset semantic description; inputting data information of a topological structure acquired by the data acquisition into a preset stack of an automat corresponding to the semantic description, the finite state set is used for indicating states included in the automat, and the input vocabulary list is used for indicating vocabularies included in the automat; mapping the data information by the automat to obtain key frames corresponding respectively to substructures and/or branches of a target object acquired by the data acquisition; and generating a visual semantic representation of the topological structure according to the key frames corresponding respectively to the substructures and/or branches of the target object acquired by the data acquisition, such that cross-media knowledge alignment is realized.

9 Claims, 3 Drawing Sheets

(58) Field of Classification Search
CPC .... G06V 10/422; G06V 20/13; G06V 30/274; G06V 30/413; G06V 10/454; G06V 10/54; G06V 10/774; G06V 10/82; G06V 30/18057; G06F 40/30; G06F 16/24575; G06F 16/2474; G06F 16/2477; G06F 16/284; G06F 9/3005; G06F 8/20; G06F 3/0486; G06F 8/34; G06F 8/38; G06F 17/28; G06F 17/30; G16H 30/40; G06T 17/00; G06T 11/006; G06T 2207/10081; G06T 2207/30004; G06T 2211/428; G06T 2207/10116; G06T 2207/20076; G06T 2207/20081; G06T 2207/30061; G06T 2207/30096; G06T 7/0012; G06T 2207/10032; G06T 2207/30181; G06T 7/11; G06T 7/174; G06T 3/4046; G06T 5/60; G06T 9/002; G06T 2207/20084; Y10S 707/99931; Y10S 128/925; G06N 3/02; G06N 3/08–088; G06N 3/0445; G06N 3/0454; G06N 3/4046; G06N 7/00; G06N 7/01; G06N 20/00; G06K 7/1482
See application file for complete search history.

(56) References Cited

U.S. PATENT DOCUMENTS

| | | | | |
|---|---|---|---|---|
| 2006/0167835 | A1* | 7/2006 | Aggarwal | G06F 16/438 |
| 2007/0239314 | A1* | 10/2007 | Kuvich | G06V 10/454 |
| | | | | 700/245 |
| 2012/0124029 | A1* | 5/2012 | Kant | G06F 16/489 |
| | | | | 707/715 |
| 2015/0332111 | A1* | 11/2015 | Kisilev | G16H 70/20 |
| | | | | 382/131 |
| 2017/0344822 | A1* | 11/2017 | Popescu | G06F 16/5838 |
| 2020/0301675 | A1* | 9/2020 | Anicic | G06F 8/34 |
| 2020/0364536 | A1* | 11/2020 | Meyer Rojas | G06N 3/04 |
| 2021/0090694 | A1* | 3/2021 | Colley | G16H 15/00 |
| 2021/0182498 | A1* | 6/2021 | Sun | G06F 40/40 |
| 2021/0216545 | A1 | 7/2021 | Fusco et al. | |
| 2023/0229824 | A1* | 7/2023 | Goyet | G06F 30/17 |
| | | | | 703/6 |
| 2023/0410487 | A1* | 12/2023 | Zhang | G06V 20/46 |
| 2024/0176998 | A1* | 5/2024 | Yao | G06T 1/20 |
| 2024/0212341 | A1* | 6/2024 | Fathi | G06V 20/10 |

* cited by examiner

```
┌─────────────────────────────────────────────────────────────────┐
│ Perform data acquisition according to a preset semantic         │
│ description, wherein the semantic description includes a finite │ ─── S101
│ semantic production set, the finite semantic production set     │
│ includes a plurality of semantic sentences, each of the         │
│ plurality of semantic sentences is configured to indicate a     │
│ topological structure of a target object to be acquired by the  │
│ data acquisition, the topological structure includes            │
│ substructures of the target object and branches included in the │
│ substructures, and the semantic sentences are a first kind of   │
│ media representation mode                                       │
└─────────────────────────────────────────────────────────────────┘
                                │
                                ▼
┌─────────────────────────────────────────────────────────────────┐
│ Input data information of the topological structure acquired by │
│ the data acquisition into a preset stack of an automat          │ ─── S102
│ corresponding to the semantic description, wherein the automat  │
│ is configured to perform cross-media knowledge mapping, and     │
│ includes a finite state set, an input vocabulary list and the   │
│ stack, the finite sate set is used for indicating states        │
│ included in the automat, and the input vocabulary list is used  │
│ for indicating vocabularies included in the automat             │
└─────────────────────────────────────────────────────────────────┘
                                │
                                ▼
┌─────────────────────────────────────────────────────────────────┐
│ Map the data information by the automat to obtain key frames    │ ─── S103
│ corresponding respectively to the substructures and/or the      │
│ branches of the target object acquired by the data acquisition  │
└─────────────────────────────────────────────────────────────────┘
                                │
                                ▼
┌─────────────────────────────────────────────────────────────────┐
│ Generate visual semantic representation of the topological      │
│ structure according to the key frames corresponding             │ ─── S104
│ respectively to the substructures and/or branches of the target │
│ object acquired by the data acquisition, wherein the visual     │
│ semantic representation is a second kind of media               │
│ representation mode                                             │
└─────────────────────────────────────────────────────────────────┘
```

FIG. 1

CROSS-MEDIA KNOWLEDGE SEMANTIC REPRESENTATION METHOD AND APPARATUS

CROSS-REFERENCE TO RELATED APPLICATIONS

The present application is a continuation of International Application No. PCT/CN2022/099377, filed on Jun. 17, 2022, the content of which is incorporated herein by reference in its entirety.

TECHNICAL FIELD

The present disclosure belongs to the field of artificial intelligence, and in particular to a cross-media knowledge semantic representation method and apparatus.

BACKGROUND

Cross-media knowledge alignment is to identify a corresponding relation between sub-branches/elements of different media, the cross-media knowledge alignment is responsible for finding the corresponding relation between the sub-branches/elements of different pieces of media information from the same target object, and the corresponding relation may be time-dimensional or spatially dimensional. Cross-media knowledge mapping is to map information in certain specific media data to another media. Cross-media knowledge alignment is to identify the corresponding relation between components and elements of different media. Cross-media fusion is to combine information of a plurality of media for target prediction (classification or regression). Cross-media collaborative learning is to transfer knowledge learned from information-rich media to information-poor media, so that learning of various media may assist each other.

At present, a knowledge representation between cross-media is realized by model training, which requires a large number of training samples and has low processing efficiency and limited accuracy.

SUMMARY

The present disclosure provides a cross-media knowledge semantic representation method and apparatus.

A first aspect of embodiments of the present disclosure provides a cross-media knowledge semantic representation method, including:

performing data acquisition according to a preset semantic description, wherein the semantic description includes a finite semantic production set, the finite semantic production set includes a plurality of semantic sentences, each semantic sentence is used for indicating a topological structure of a target objected to be acquired by the data acquisition, the topological structure includes substructures of the target object and branches included in the substructures, and each semantic sentence is a first kind of media representation mode;

inputting data information of the topological structure acquired by the data acquisition to a preset stack of an automat corresponding to the semantic description, wherein the automat is configured to perform cross-media knowledge mapping, and includes a finite state set, an input vocabulary list and the stack, the finite state set is used for indicating states included in the automat, and the input vocabulary list is used for indicating vocabularies included in the automat;

mapping the data information by the automat to obtain key frames corresponding respectively to the substructures and/or the branches of the target object acquired by the data acquisition; and generating a visual semantic representation of the topological structure according to the key frames corresponding respectively to the substructures and/or branches of the target object acquired by the data acquisition, wherein the visual semantic representation is a second kind of media representation mode.

In an embodiment, an expression of the semantic description G is:

$$G=(V,T,P,S_0);$$

V is a finite semantic production set;

T is a finite vocabulary set, and V and T do not intersect;

$S_0$ is a starting variable of the semantic description G, $S_0 \in V$; and

P is a finite semantic production set, the finite semantic production set includes a plurality of productions, each production is represented as $A \to \alpha$, A is a semantic variable, $A \in V$, and $\alpha$ is a string of semantic variables and vocabularies in a set $(V \cup T)^*$.

In an embodiment, an expression of the automat M is:

$$M=(Q,\Sigma,\Gamma,\delta,q_0,Z_0,F);$$

Q is a finite state set;

$\Sigma$ is an input vocabulary list;

$\Gamma$ is a stack alphabet;

$\delta$ is mapping from $Q \times (\Sigma \cup \{\varepsilon\}) \times \Gamma$ to a finite subset $Q \times \Gamma^*$, $\varepsilon$ represents vocabulary vacancy, and $\Gamma^*$ is any combination of the stack alphabet;

$q_0$ is an initial state, $q_0 \in Q$;

$Z_0 \in \Gamma$ is an initial letter of the stack alphabet; and

F is a termination state set, $F \subseteq Q$.

In an embodiment, mapping the data information by the automat to obtain key frames corresponding respectively to the substructures and/or the branches of the target object acquired by the data acquisition includes:

obtaining a current state of the automat; and when the current state is within a state included in the finite state set Q, obtaining data information currently inputted into the stack of the automat, if the data information currently inputted into the stack of the automat belongs to vocabularies in the input vocabulary list $\Sigma$ and a stack letter Z is on a stack top, generating a character string $\gamma$ according to the data information in the stack, the character string $\gamma$ being able to be used for generating the key frames corresponding respectively to the substructures and/or the branches of the target object respectively, and replacing the stack letter Z with the character string $\gamma$, the automat entering in a new state until the new state is within the state included in the termination state set F or the stack is empty, $\gamma \in \Gamma^*$, $Z \in \Gamma$, and the stack letter Z referring to all pieces of data information generating a visual semantic representation corresponding to the previous topological structure.

In an embodiment, the method further includes:

If the data information currently inputted into the stack of the automat is the vocabulary vacancy, the automat not processing the data information in the stack and entering in the new state until the new state is within the state included in the termination state set F or the stack is empty.

In an embodiment, the cross-media knowledge semantic representation method is applied to ultrasonic scanning, the topological structure of the target object refers to an anatomical structure of medical tissue, the data information is a tomography scanning image of each part of the anatomical structure, the first kind of media representation mode is a semantic description of scanning tomography, and the second kind of media representation mode is a three-dimensional medical image corresponding to the anatomical structure of the medical tissue.

In an embodiment, the performing data acquisition according to a preset semantic description includes:

performing data acquisition by adopting an ultrasonic scanner according to the preset semantic description.

A second aspect of the embodiments of the present disclosure provides a cross-media knowledge semantic representation apparatus, including a memory and one or more processors, wherein the memory stores an executable code, and the executable code, when executed by the one or more processors, is used for implementing the cross-media knowledge semantic representation method according to any of the above embodiments.

A third aspect of the embodiments of the present disclosure provides a computer readable storage medium, storing a program, the program, when executed by a processor, implementing the cross-media knowledge semantic representation method according to any of the above embodiments.

The present disclosure has the beneficial effects: the semantic description is combined with automat to implement automatic mapping of knowledge of the first kind of media representation mode to knowledge of the second kind of media representation mode, so as to realize the cross-media knowledge alignment, identify the corresponding relation between multilevel components (topological structures) of different media, and achieve a high processing efficiency, and a high accuracy.

BRIEF DESCRIPTION OF DRAWINGS

FIG. 1 is a schematic flow diagram of a cross-media knowledge semantic representation method according to an embodiment of the present disclosure.

DESCRIPTION OF EMBODIMENTS

Technical solutions of embodiments of the present disclosure will be clearly and completely described below in conjunction with accompanying drawings in the embodiments of the present disclosure.

The embodiments of the present disclosure realize automatic mapping of knowledge of the first kind of media representation mode to knowledge of the second kind of media representation mode by combining the semantic description and automat, accordingly the cross-media knowledge alignment is realized, the corresponding relation between multilevel components (topological structures) of different media is identified, processing efficiency is high, and accuracy is high.

A cross-media knowledge semantic representation method of an embodiment of the present disclosure may be applied to ultrasonic scanning, anatomy knowledge semantics corresponding to a medical tomography scanning image (picture or video streaming) of an anatomical structure of medical tissue are described through semantic description, to realize data acquisition, and the acquired medical tomography scanning image of the anatomical structure of the medical tissue is mapped to a three-dimensional medical image of the medical tissue by the automat so as to align non-visualized medical tomography scanning images to a visual three-dimensional medical image of the medical tissue. It should be understood that the cross-media knowledge semantic representation method of the embodiment of the present disclosure may also be applied to other fields, for example, internal structure evaluation of parts in a machine machining process.

An embodiment of the present disclosure provides a cross-media knowledge semantic representation method, and an execution body of the cross-media knowledge semantic representation method of the embodiment of the present disclosure may be any device with a data processing capability, such as a computer, a mobile phone and other terminal devices.

Referring to FIG. 1, the cross-media knowledge semantic representation method of the embodiment of the present disclosure may include steps S101-S104.

In step S101, data acquisition is performed according to a preset semantic description, wherein the semantic description includes a finite semantic production set, the finite semantic production set includes a plurality of semantic sentences, each semantic sentence is used for indicating a topological structure of a target object to be acquired by the data acquisition, the topological structure includes substructures of the target object and branches included in the substructures, and each semantic sentence is a first kind of media representation mode.

Figure 2:
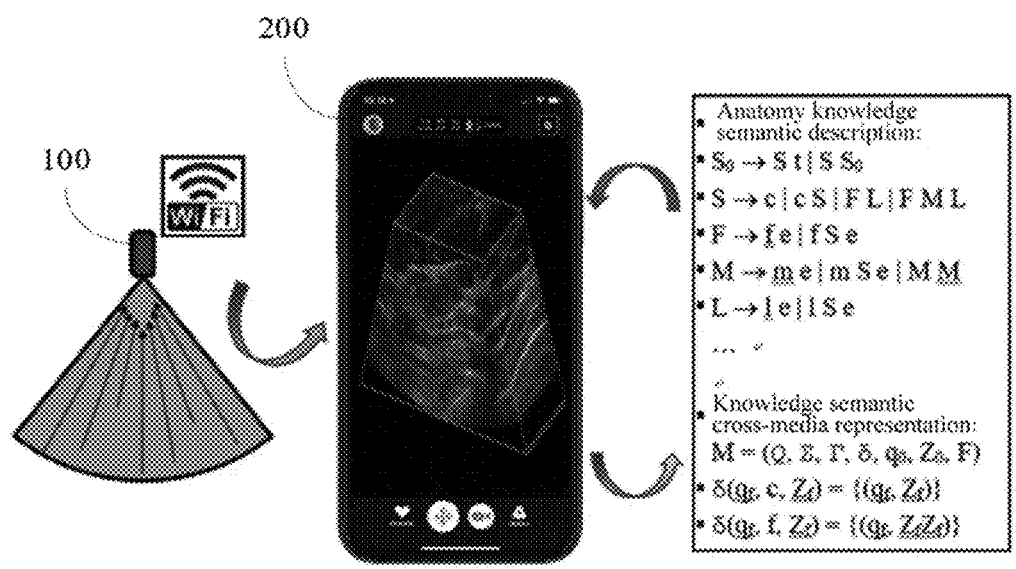
FIG. 2 is a schematic diagram of an application scenario of a cross-media knowledge semantic representation method according to an embodiment of the present disclosure.

For example, referring to FIG. 2, the cross-media knowledge semantic representation method is applied to ultrasonic scanning, the target object is a user to be ultrasonically scanned, the topological structure is an anatomical structure of medical tissue of the user, the medical tissue may be such as a heart, a biliary system, a liver or a kidney. For example, taking the medical tissue being the heart as an example, the anatomical structure of the heart may include heart->left atrium->lumen, intima and myocardium; and heart->right atrium->lumen, intima and myocardium.

Following the embodiment of applying the cross-media knowledge semantic representation method to ultrasonic scanning, specifically, the step S101 is to perform data acquisition by adopting an ultrasonic scanner (referring to FIG. 2) according to the present semantic description. The embodiment of the present disclosure does not specifically limit the type of the ultrasonic scanner, for example, the ultrasonic scanner may be a B-mode ultrasound scanning probe, and may also be ultrasonic scanners of other types.

Data information of the topological structure acquired by the ultrasonic scanner may include a tomography scanning image of each part (one topological structure may include a plurality of parts, and each part may be a substructure of branch) of the topological structure, the first kind of media representation mode is the semantic description of scanning tomography, the semantic description of the scanning tomography may not be comprehensible to a non-ultrasound scanning medical worker, and therefore, non-visualized medical tomography scanning images need to be aligned, by the automat, to a three-dimensional medical image corresponding to the anatomical structure of the medical tissue able to be understood by the non-ultrasound scanning medical worker.

Exemplarily, referring to FIG. 2, an execution body of a cross-media knowledge semantic representation method is a mobile phone 200, an ultrasonic scanning medical worker performs scanning through a B-mode ultrasound scanning probe 100 to obtain a medical tomography scanning image of a topological structure of a target anatomical structure according to a preset semantic description, a medical tomography scanning image of a topological structure of a certain anatomical structure obtained by the B-mode ultrasound scanning probe 100 through scanning may be transmitted to an APP (a three-dimensional medical image shown on the mobile phone 200 in FIG. 2) installed on the mobile phone 200 through WiFi or other transmission modes, the semantic description of one anatomy defines the anatomical structure (anatomy knowledge semantic description in FIG. 2, one row represents a semantic sentence) of the medical tissue and is input to the APP, one semantic sentence is equivalent to an instruction to indicate the B-mode ultrasound scanning probe 100 to perform the data acquisition, and the medical tomography scanning image of the corresponding topological structure is obtained.

The semantic sentences in the embodiment of the present disclosure define the topological structure of the target anatomical structure, and a grapheme of each semantic sentence may indicate the ultrasonic scanning medical worker to obtain the tomography scanning image of the corresponding part with the B-mode ultrasound scanning probe through the APP and extract a segmentation boundary point. For example, the semantic sentence is displayed directly on a display interface of the APP, indicating that the ultrasonic scanning medical worker uses the B-mode ultrasound scanning probe to obtain the tomography scanning image of the corresponding part and extract the segmentation boundary point. In the embodiment of the present disclosure, the segmentation boundary point is used to indicate a boundary of each part in the anatomical structure.

The semantic description may be defined in advance by the user, and specifically, in some embodiments, the expression of the semantic description G is:

$$G = (V, T, P, S_0) \quad (1);$$

in the formula (1), V is a finite semantic production set; T is a finite vocabulary set, and V and T do not intersect; $S_0$ is a starting variable of the semantic description G, $S_0 \in V$; and P is a finite semantic production set, the finite semantic production set includes a plurality of productions, each production is represented as $A \to \alpha$, A is a semantic variable, $A \in V$, and $\alpha$ is a string of semantic variables and vocabularies in a set $(V \cup T)^*$.

Exemplarily, an anatomy knowledge semantic description grammar $G_{pd} = (V, T, P, S_0)$ is implemented, and $G_{pd}$ is represented on the basis of semantic knowledge of an anatomical structure of a set of tomography scanning images:

$$V = \{S_0, S, F, M, L\};$$

$$T = \{c, f, m, l, e, t\};$$

P includes:
$S_0 \to S\ t | S\ S_0$;
$S \to c | c\ S | F\ L | F\ M\ L$;
$F \to f\ e | f\ S\ e$;
$M \to m\ e | m\ S\ e | M\ M$;
$L \to l\ e | l\ S\ e$; and a semantic symbol on the left of "$\to$" may be replaced by any semantic string on two sides of "|".

A variable in V corresponds to an tissue structure or substructure that has one of the following semantics:
$S_0$, one tomography scanning;
S, one tissue structure or substructure including a single branch or a plurality of branches;
F, a first branch of the plurality of branches;
L, the last branch of the plurality of branches; and
M, other branches of the plurality of branches (except the first branch and the last branch).

Except t, the grapheme in T corresponds to a section of the tissue structure or substructure, and t represents a termination of the description of the tissue structure or substructure, and semantics of the other graphemes are as follows:
c, a continuous tomography scanning image section on a main structure or branch;
f, a first section on the first branch;
l, the last section on the first branch;
m, a first section (except the first branch and the last branch) of other branches of the plurality of branches; and
e, the last section (availability of an actual section is optional) on the branches.

$G_{pd}$ describes development of branching and merging in the anatomical structure of the medical tissue, which decides the kind of topological structure able to be described (the kind of topological structure may be interpreted by the automat), and each semantic sentence derived from $G_{pd}$ is a description of one anatomical structure. Although the geometry of the anatomical structure may change, the topological structure of the anatomical structure remains constant, so $G_{pd}$ uses recursive definitions of the substructures and branches of the anatomical structure, and $G_{pd}$ may describe very complex topological structures (e.g., a gallbladder and a bile duct).

An example of the topological structure of the anatomical structure is as follows:
$S_0 \Rightarrow S\ S_0 \Rightarrow c\ S\ S_0 \Rightarrow c\ c\ S_0 \Rightarrow c\ c\ S\ S_0$;
$\Rightarrow c\ c\ F\ L\ S_0 \Rightarrow c\ c\ c\ f\ e\ L\ S_0 \Rightarrow c\ c\ f\ e\ l\ e\ S_0$;
$\Rightarrow c\ c\ f\ e\ l\ e\ S\ S0 \Rightarrow c\ c\ f\ e\ l\ e\ F\ M\ L\ S0 \Rightarrow c\ c\ f\ e\ l\ e\ f\ e\ M\ L\ S0$;
$\Rightarrow c\ c\ f\ e\ l\ e\ f\ e\ m\ e\ L\ S0 \Rightarrow c\ c\ f\ e\ l\ e\ f\ e\ m\ e\ l\ e\ S0$;
$\Rightarrow c\ c\ f\ e\ l\ e\ f\ e\ m\ e\ l\ e\ S\ t \Rightarrow c\ c\ f\ e\ l\ e\ f\ e\ m\ e\ l\ e\ F\ L\ t$;
$\Rightarrow c\ c\ f\ e\ l\ e\ f\ e\ m\ e\ l\ e\ f\ S\ e\ L\ t \Rightarrow c\ c\ f\ e\ l\ e\ f\ e\ m\ e\ l\ e\ f\ c\ e\ L\ t$;
$\Rightarrow c\ c\ f\ e\ l\ e\ f\ e\ m\ e\ l\ e\ f\ c\ e\ l\ S\ e\ t$; and
$\Rightarrow c\ c\ f\ e\ l\ e\ f\ e\ m\ e\ l\ e\ f\ c\ e\ l\ c\ e\ t$.

In step S102, the data information of the topological structure obtained by the data acquisition is inputted into a preset stack of an automat corresponding to the semantic description, wherein the automat is configured to perform cross-media knowledge mapping, and includes a finite state set, an input vocabulary list and the stack, the finite state set is used for indicating states included in the automat, and the input vocabulary list is used for indicating vocabularies included in the automat.

In some embodiments, an expression of the automat M is:

$$M = (Q, \Sigma, \Gamma, \delta, q_0, Z_0, F) \quad (2);$$

in the formula (2), Q is a finite state set;
$\Sigma$ is an input vocabulary list;
$\Gamma$ is a stack alphabet;

$\delta$ is mapping from $Q\times(\Sigma\cup\{\varepsilon\})\times\Gamma$ to a finite subset $Q\times\Gamma^*$, $\varepsilon$ represents vocabulary vacancy, and $\Gamma^*$ is any combination of the stack alphabet;

$q_0$ is an initial state, $q_0\in Q$;

$Z_0\in\Gamma$ is an initial letter of the stack alphabet; and

F is a termination state set, $F\subseteq Q$.

In the step, the automat M corresponds to the semantic description G in the step S101.

In step S103, the data information is mapped by the automat to obtain key frames corresponding respectively to the substructures and/or the branches of the target object acquired by the data acquisition.

Specifically, mapping the data information by the automat to obtain the key frames corresponding respectively to the substructures and/or the branches of the target object acquired by the data acquisition may include but is not limited to the following steps:

S1031, executing mapping from $Q\times(\Sigma\cup\{\varepsilon\})\times\Gamma$ to the finite subset $Q\times\Gamma^*$ from the initial state $q_0\in Q$, to obtain a current state q of the automat; and S1032, when the current state q is within a state included in the finite state set Q (namely, $q\in Q$), obtaining data information $Z\in\Gamma$ currently inputted into the stack of the automat, if the data information currently inputted into the stack of the automat belongs to vocabularies in the input vocabulary list $\Sigma$ and a stack letter Z is on a stack top, generating a character string $\gamma$ according to the data information in the stack, $\gamma\in\Gamma^*$, the character string $\gamma$ being able to be used for generating the key frames corresponding respectively to the substructures and/or the branches of the target object, and replacing the stack letter Z with the character string $\gamma$, the automat entering in a new state until the new state is within the state included in the termination state set F or the stack is empty, and the stack letter Z referring to all pieces of data information generating a visual semantic representation corresponding to the previous topological structure.

Furthermore, in some embodiments, the cross-media knowledge semantic representation method may further include the following steps: when the current state is within the state included in the finite state set Q, the data information currently inputted into the stack of the automat is obtained, if the data information currently inputted into the stack of the automat is the vocabulary vacancy c, the automat not processing the data information in the stack and entering the new state until the new state is within the state included in the termination state set F or the stack is empty.

In a feasible implementation, a process of mapping the data information by the automat is as follows:

(1), the initial state of the automat M is set as $q_0$;

(2), when a condition (the current state $q\in Q$ of the automat M) is met, {is circularly executed;

(3), when a condition (the data information $a\in\Sigma$ currently inputted into the stack of the automat, and the stack letter $Z\in\Gamma$ is on the stack top) is met, {is executed;

(4), the automat M enters in the new state $q\in Q$;

(5), the character string $\gamma\in\Gamma^*$ replaces the stack letter Z};

(6), otherwise, if (the data information $a=\varepsilon$ currently inputted into the stack of the automat), {is executed;

(7), the automat M ignores input vocabularies, and enters the new state $q\in Q$;

(8), the character string $\gamma\in\Gamma^*$ replaces the stack letter Z};

(9), if (the new state $q\in F$, or the stack becomes empty); and (10), shutdown.

(11), otherwise, (12), a circulation } is continuously executed.

Corresponding to $G_{pd}$ in the above embodiment, the corresponding automat $M_{tg}$ may be used for interpreting the semantic sentences derived from $G_{pd}$:

$M_{tg}=(Q,\Sigma,\Gamma,\delta,q_0,Z_0,\varphi)$;

$Q=\{q_0, q_s, q_b, q_f, q_m, q_l, q_e\}$;

$Z=\{c, f, m, l, e, t\}$, $\Gamma=\{Z_0, Z_s, Z_f, Z_m, Z_l\}$;

$F=\varphi$; and $\delta$ is mapping from $Q\times(\Sigma\cup\{\varepsilon\})\times\Gamma$ to the finite subset $Q\times\Gamma^*$;

$\delta(q_0, t, Z_0)=\{(q_0, \varepsilon)\}$, $\delta(q_s, c, Z_s)=\{(q_s, Z_s)\}$;

$\delta(q_0, c, Z_0)=\{(q_s, Z_s)\}$, $\delta(q_s, f, Z_s)=\{(q_f, Z_fZ_s)\}$;

$\delta(q_0, f, Z_0)=\{(q_f, Z_fZ_0)\}$;

$\delta(q_f, c, Z_f)=\{(q_f, Z_f)\}$;

$\delta(q_f, f, Z_f)=\{(q_f, Z_fZ_f)\}$;

$\delta(q_f, e, Z_f)=\{(q_b, \varepsilon)\}$;

$\delta(q_b, m, Z_0)=\{(q_m, Z_mZ_0)\}$, $\delta(q_b, l, Z_0)=\{(q_l, Z_lZ_0)\}$;

$\delta(q_b, m, Z_s)=\{(q_m, Z_mZ_s)\}$, $\delta(q_b, l, Z_s)=\{(q_l, Z_lZ_s)\}$;

$\delta(q_b, m, Z_f)=\{(q_m, Z_mZ_f)\}$, $\delta(q_b, l, Z_f)=\{(q_l, Z_lZ_f)\}$;

$\delta(q_b, m, Z_m)=\{(q_m, Z_mZ_m)\}$, $\delta(q_b, l, Z_m)=\{(q_l, Z_lZ_m)\}$;

$\delta(q_b, m, Z_l)=\{(q_m, Z_mZ_l)\}$, $\delta(q_b, l, Z_l)=\{(q_l, Z_lZ_l)\}$;

$\delta(q_m, c, Z_m)=\{(q_m, Z_m)\}$, $\delta(q_l, c, Z_l)=\{(q_l, Z_l)\}$;

$\delta(q_m, f, Z_m)=\{(q_f, Z_fZ_m)\}$, $\delta(q_l, f, Z_l)=\{(q_f, Z_fZ_l)\}$;

$\delta(q_m, e, Z_m)=\{(q_b, \varepsilon)\}$, $\delta(q_l, e, Z_l)=\{(q_e, \varepsilon)\}$;

$\delta(q_e, \varepsilon, Z_0)=\{(q_0, Z_0)\}$;

$\delta(q_e, \varepsilon, Z_s)=\{(q_s, Z_s)\}$;

$\delta(q_e, \varepsilon, Z_f)=\{(q_f, Z_f)\}$;

$\delta(q_e, \varepsilon, Z_m)=\{(q_m, Z_m)\}$; and $\delta(q_e, \varepsilon, Z_l)=\{(q_l, Z_l)\}$.

The automat $M_{tg}$ reads a terminal character string (the character string $\gamma$ includes the terminal character string) representing the tomography scanning image in sequence, and a mapping operation $\delta$ is adopted from the mapping set from the $Q\times(\Sigma\cup\{\varepsilon\})\times\Gamma$ to the finite subset $Q\times\Gamma^*$ to generate key framed according to the current state, the current input character (that is, the data information currently inputted into the stack of the automat), and the current stack top letter. The empty stack is used as a signal to successfully interpret the semantic description of the topological structure, so the final state ($F=\varphi$) is not clearly defined. A stack letter $Z\in\{Z_0, Z_s, Z_f, Z_m, Z_l\}$ refers to all pieces of information able to be used for generating the current tomography scanning image in the previous tomography scanning image.

Referring to FIG. 2, an APP is also inputted into the automat corresponding to the semantic description, and the automat is used for interpreting and generating the scanning tomography, which is matched with the three-dimensional medical image (the knowledge semantic cross-media representation in FIG. 2) to generate the key frames (i.e., the key images) of the anatomical structure of the medical tissue.

In step S104, a visual semantic representation of the topological structure is generated according to the key frames corresponding respectively to the substructures and/or branches of the target object acquired by the data acquisition, wherein the visual semantic representation is a second kind of media representation mode.

Exemplarily, the cross-media knowledge semantic representation method is applied to ultrasonic scanning, the topological structure of the target object refers to the anatomical structure of the medical tissue, the data information is the tomography scanning image of each part of the anatomical structure, the first kind of media representation mode is a semantic description of scanning tomography, and the second kind of media representation mode is a three-dimensional medical image corresponding to the anatomical structure of the medical tissue. The cross-media knowledge semantic representation method of the embodiment of the present disclosure is used to align non-visualized medical tomography scanning images to a three-dimensional medical image corresponding to the anatomical structure of the medical tissue able to be understood by a non-ultrasonic scanning medical worker.

Corresponding to the embodiment of the cross-media knowledge semantic representation method, the present disclosure further provides an embodiment of a cross-media knowledge semantic representation apparatus.

Figure 3:
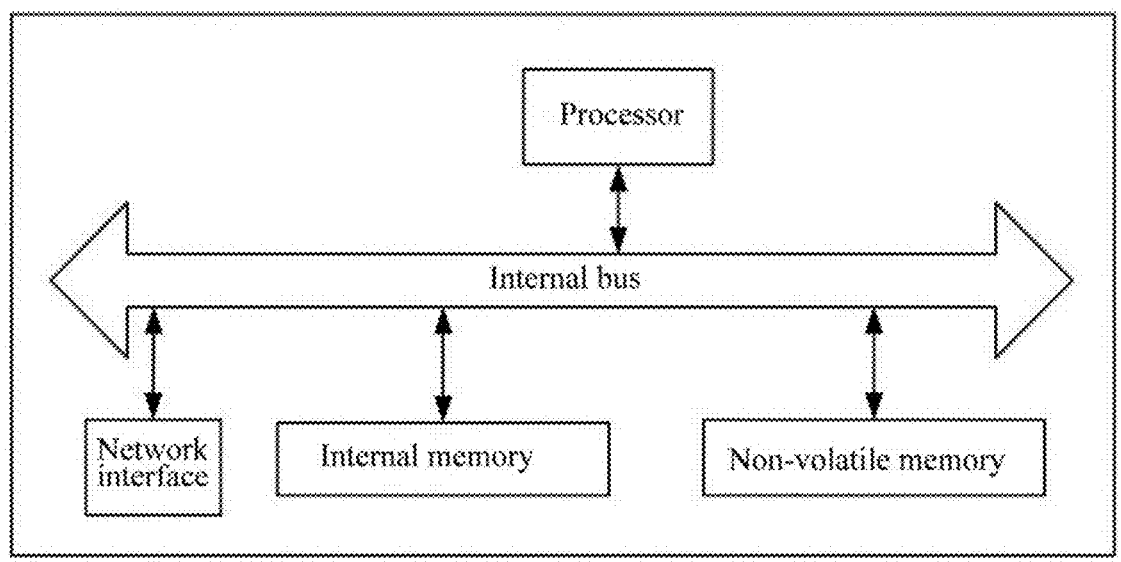
FIG. 3 is a structural block diagram of a cross-media knowledge semantic representation apparatus according to an embodiment of the present disclosure.

Referring to FIG. 3, the cross-media knowledge semantic representation apparatus according to an embodiment of the present disclosure includes a memory and one or more processors, the memory stores an executable code, and the executable code, when executed by the one or more processors, is used for implementing the cross-media knowledge semantic representation method in the above embodiment.

The embodiment of the cross-media knowledge semantic representation apparatus according to an embodiment of the present disclosure may be applied to any device with data processing capability, any device with the data processing capability may be a device or apparatus like a computer. The embodiment of the apparatus may be realized by software, or by hardware or a combination of hardware and software. Taking software implementation as an example, as a logical apparatus, it is formed by reading and running a corresponding computer program instruction in a non-volatile memory into an Internal memory through a processor of any device with the data processing capability. From the hardware level, FIG. 3 shows a hardware structural diagram of any device with the data processing capability in which the cross-media knowledge semantic representation apparatus according to an embodiment of the present disclosure is located, and except for the processor, the Internal memory, a network interface and the non-volatile memory shown in FIG. 3, any device with the data processing capability in which the apparatus in the embodiment is located may also include other hardware according to the actual function of the device with data processing capability, which is not described in detail.

The implementation process of the functions and roles of each unit in the above apparatus refers to details in the implementation process of the corresponding steps in the above method, which is not repeated here.

For the apparatus embodiment, since it basically corresponds to the method embodiment, the relevant points may be referred to part of the description of the method embodiment. The apparatus embodiment described above is schematic only, units described as separate components may be physically separate or not, and components shown as units may be physical units or not, that is, may be located in one place, or may be distributed on a plurality of network units. Part or all of modules may be selected according to actual needs to realize the purpose of solutions of the present disclosure. Those ordinarily skilled in the art may understand and implement the purpose without creative effort.

An embodiment of the present disclosure further provides a computer readable storage medium, storing a program, and the program, when executed by a processor, implements the cross-media knowledge semantic representation method in the above embodiment.

The computer readable storage medium may be an Internal memory unit of any device with the data processing capability of the any above embodiment, such as a hard disk or Internal memory. The computer readable storage medium may also be an external storage device of any device with the data processing capability, such as a plug-in hard disk, a smart media card (SMC), an SD card, a flash card, etc., equipped on the device. Further, the computer readable storage medium may further include both the Internal memory unit of any device with the data processing capability and the external storage device. The computer readable storage medium is used for storing the computer program and other programs and data required by any device with the data processing capability, and may also be used for temporarily storing data that has been outputted or will be outputted.

The above is only preferred embodiments of the present disclosure and is not intended to limit the present disclosure, and for those skilled in the art, the present disclosure may have various changes and variations. Any modification, equivalent replacement, improvement, etc. made within the spirit and principle of the present disclosure shall fall within the scope of protection of the present disclosure.

What is claimed is:

1. A cross-media knowledge semantic representation method, comprising:
performing data acquisition according to a preset semantic description, wherein the semantic description comprises a finite semantic production set, and the finite semantic production set comprises a plurality of semantic sentences, each of the plurality of semantic sentences is configured to indicate a topological structure of a target object to be acquired by the data acquisition, the topological structure comprises substructures of the target object and branches comprised in the substructures, and the semantic sentences are a first kind of media representation mode;
inputting data information of the topological structure acquired by the data acquisition into a preset stack of an automat corresponding to the semantic description, wherein the automat is configured to perform cross-media knowledge mapping, and comprises a finite state set, an input vocabulary list and the stack, the finite state set is used for indicating states comprised in the automat, and the input vocabulary list is used for indicating vocabularies comprised in the automat;
mapping the data information by the automat to obtain key frames corresponding to the substructures and/or the branches of the target object acquired by the data acquisition, respectively; and
generating a visual semantic representation of the topological structure according to the key frames corresponding to the substructures and/or branches of the target object acquired by the data acquisition, respectively, wherein the visual semantic representation is a second kind of media representation mode.

2. The cross-media knowledge semantic representation method according to claim 1, wherein the semantic description G is expressed by:

$$G=(V,T,P,S_0);$$

where V is a finite semantic production set;
T is a finite vocabulary set, wherein V and T do not intersect each other;
$S_0$ is a starting variable of the semantic description G, $S_0 \in V$; and
P is a finite semantic production set, the finite semantic production set comprises a plurality of productions, each of the plurality of productions is represented as $A \to \alpha$, A is a semantic variable, $A \in V$, and $\alpha$ is a string of semantic variables and vocabularies in a set $(V \cup T)^*$.

3. The cross-media knowledge semantic representation method according to claim 1, wherein the automat M is expressed by:

$$M=(Q,\Sigma,\Gamma,\delta,q_0,Z_0,F);$$

where Q is a finite state set;
$\Sigma$ is an input vocabulary list;
$\Gamma$ is a stack alphabet;
$\delta$ is mapping from $Q\times(\Sigma\cup\{\varepsilon\})\times\Gamma$ to a finite subset $Q\times\Gamma^*$, $\varepsilon$ represents vocabulary vacancy, and $\Gamma^*$ is any combination of the stack alphabet;
$q_0$ is an initial state, $q_0\in Q$;
$Z_0\in\Gamma$ is an initial letter of the stack alphabet; and
F is a termination state set, $F\subseteq Q$.

4. The cross-media knowledge semantic representation method according to claim 3, wherein said mapping the data information by the automat to obtain key frames corresponding to the substructures and/or the branches of the target object acquired by the data acquisition, respectively, comprises:
obtaining a current state of the automat; and
when the current state is within a state comprised in the finite state set Q, obtaining data information currently inputted into the stack of the automat, when the data information currently inputted into the stack of the automat belongs to vocabularies in the input vocabulary list $\Sigma$ and a stack letter Z is on a stack top, generating a character string $\gamma$ according to the data information in the stack, wherein the character string $\gamma$ is capable of generating the key frames corresponding to the substructures and/or the branches of the target object, respectively, and replacing the stack letter Z with the character string $\gamma$, and the automat enters a new state until the new state is within a state comprised in the termination state set F or until the stack is empty, $\gamma\in\Gamma^*$, $Z\in\Gamma$, and wherein the stack letter Z refers to all data information for generating a visual semantic representation corresponding to the previous topological structure.

5. The cross-media knowledge semantic representation method according to claim 4, wherein
when the data information currently inputted into the stack of the automat is the vocabulary vacancy, the automat does not process the data information in the stack, but enters in the new state until the new state is within the state comprised in the termination state set F or until the stack is empty.

6. The cross-media knowledge semantic representation method according to claim 1, wherein the cross-media knowledge semantic representation method is applied to ultrasonic scanning, the topological structure of the target object refers to an anatomical structure of medical tissue, the data information is a tomography scanning image of each part of the anatomical structure, the first kind of media representation mode is a semantic description of scanning tomography, and the second kind of media representation mode is a three-dimensional medical image corresponding to the anatomical structure of the medical tissue.

7. The cross-media knowledge semantic representation method according to claim 6, wherein said performing data acquisition according to a preset semantic description comprises:
performing data acquisition by adopting an ultrasonic scanner according to the preset semantic description.

8. A cross-media knowledge semantic representation apparatus, comprising a memory and one or more processors, wherein the memory stores an executable code, and the executable code, when executed by the one or more processors, is configured to implement the cross-media knowledge semantic representation method according to claim 1.

9. A non-transitory computer readable storage medium, on which a program is stored, and the program, when executed by a processor, is configured to implement the cross-media knowledge semantic representation method according to claim 1.

* * * * *